(12) United States Patent
Fukukita et al.

(10) Patent No.: US 8,641,625 B2
(45) Date of Patent: Feb. 4, 2014

(54) ULTRASONIC DIAGNOSTIC APPARATUS

(75) Inventors: Hiroshi Fukukita, Tokyo (JP); Hisashi Akiyama, Kanagawa (JP)

(73) Assignee: Panasonic Corporation, Osaka (JP)

( * ) Notice: Subject to any disclaimer, the term of this patent is extended or adjusted under 35 U.S.C. 154(b) by 347 days.

(21) Appl. No.: 12/440,533

(22) PCT Filed: Sep. 10, 2007

(86) PCT No.: PCT/JP2007/067612
§ 371 (c)(1),
(2), (4) Date: Mar. 9, 2009

(87) PCT Pub. No.: WO2008/032685
PCT Pub. Date: Mar. 20, 2008

(65) Prior Publication Data
US 2010/0041995 A1    Feb. 18, 2010

(30) Foreign Application Priority Data

Sep. 11, 2006   (JP) .................................. 2006-245223

(51) Int. Cl.
*A61B 8/00* (2006.01)
(52) U.S. Cl.
USPC ............. 600/447; 600/437; 600/459; 73/625; 367/140
(58) Field of Classification Search
USPC .................................. 600/447, 443, 437, 459
See application file for complete search history.

(56) References Cited

U.S. PATENT DOCUMENTS

| | | | |
|---|---|---|---|
| 5,549,111 A * | 8/1996 | Wright et al. | 600/443 |
| 6,042,546 A * | 3/2000 | Bae | 600/447 |
| 6,186,948 B1 | 2/2001 | Kamiyama et al. | |
| 6,245,017 B1 * | 6/2001 | Hashimoto et al. | 600/447 |
| 6,468,216 B1 | 10/2002 | Powers et al. | |
| 6,544,175 B1 | 4/2003 | Newman | |
| 6,582,367 B1 * | 6/2003 | Robinson et al. | 600/443 |
| 7,914,454 B2 * | 3/2011 | Weber et al. | 600/443 |
| 2003/0045795 A1 | 3/2003 | Bjaerum et al. | |
| 2005/0228280 A1 * | 10/2005 | Ustuner et al. | 600/443 |

FOREIGN PATENT DOCUMENTS

| | | |
|---|---|---|
| JP | 59-118142 A | 7/1984 |
| JP | 2000-107182 A | 4/2000 |
| JP | 2000-139906 A | 5/2000 |

(Continued)

OTHER PUBLICATIONS

European Search Report for EP 07 80 7021 dated Apr. 20, 2011.

(Continued)

*Primary Examiner* — Tse Chen
*Assistant Examiner* — Patricia Park
(74) *Attorney, Agent, or Firm* — Pearne & Gordon LLP

(57) ABSTRACT

An object of the invention is to provide an ultrasonic diagnostic apparatus that can scan a region of interest at high speed and other regions at low speed.

In the ultrasonic diagnostic apparatus of the invention, a two-dimensional array probe 1 formed by arranging a plurality of ultrasonic elements two-dimensionally transmits an ultrasonic beam to a three-dimensional region and receives a reflected signal. The ultrasonic beam scans a region on a pyramid, and the scan region is divided into a main scan region Am of a region of interest and a subscan region. The subscan region is divided into small regions As1, As2, As3, and As4. The number of main scanning times of the main scan region is larger than the number of subscanning times of the subscan region.

5 Claims, 5 Drawing Sheets

(56) References Cited

FOREIGN PATENT DOCUMENTS

| | | |
|---|---|---|
| JP | 2003-093385 A | 4/2003 |
| JP | 2004-195024 A | 7/2004 |
| JP | 2005-185333 A | 7/2005 |
| WO | 2004/021041 A1 | 3/2004 |

OTHER PUBLICATIONS

International Search Report for PCT/JP2007/067612.

Doyle et al., Block Regional Interpolation Scheme for k-Space [BRISK]: A Rapid Cardiac Imaging Technique, Magnetic Resonance in Medicine, vol. 33, No. 2, pp. 163-170, 1996.

* cited by examiner

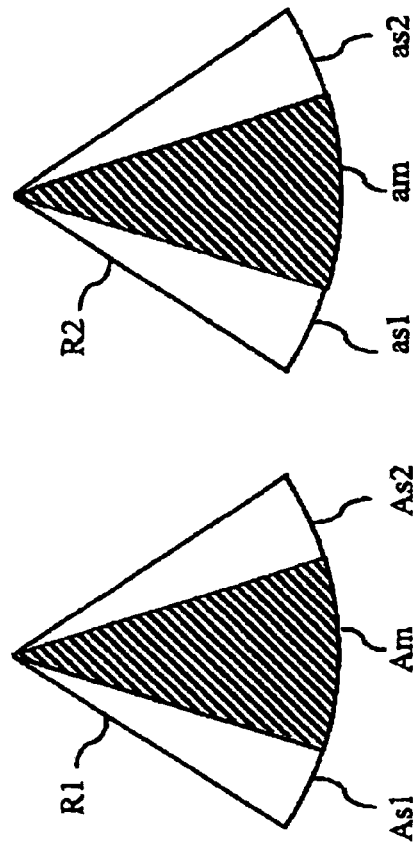
FIG. 2A
FIG. 2B
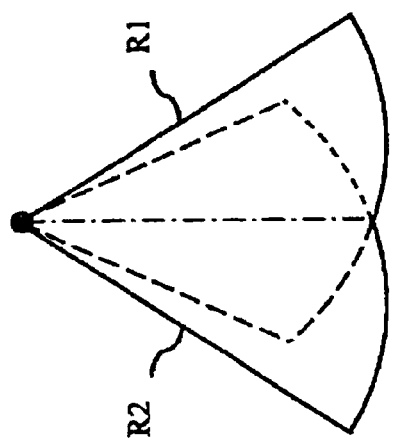
FIG. 2C
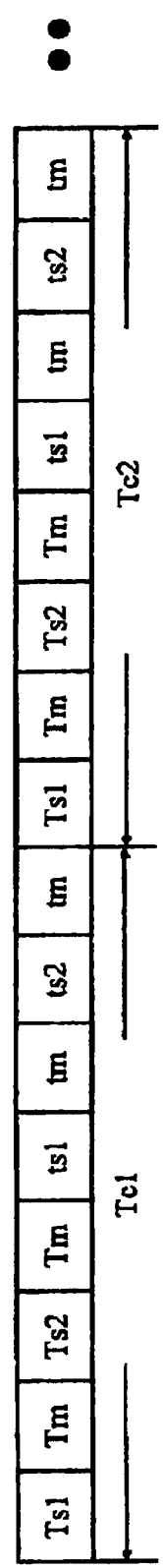

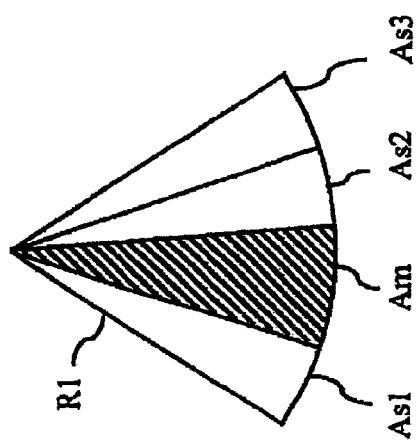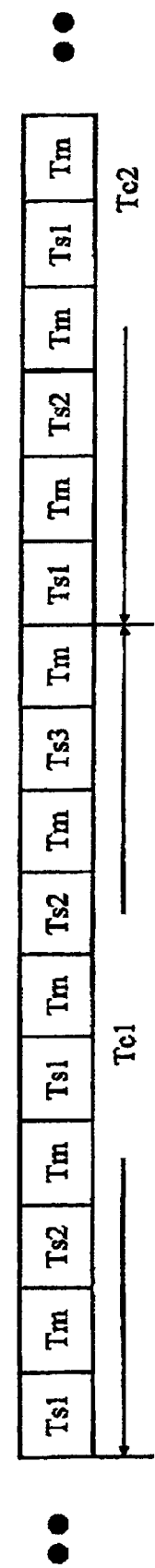
FIG. 3A
FIG. 3B

ULTRASONIC DIAGNOSTIC APPARATUS

TECHNICAL FIELD

This invention relates to an ultrasonic diagnostic apparatus for scanning a region of interest at high speed and other regions at low speed.

BACKGROUND ART

As shown in FIGS. 5A and 5B, a conventional ultrasonic diagnostic apparatus is configured so as to perform drive control of a two-dimensional array probe 1 formed by arranging a plurality of ultrasonic elements two-dimensionally so as to intermittently perform three-dimensional scanning of a target with the two-dimensional array probe. In an interval of three-dimensional scanning T3 performed intermittently, two-dimensional scanning T2 is performed at a scanning rate higher than the scanning rate at the three-dimensional scanning time and a three-dimensional image is formed based on a method obtained by the three-dimensional scanning and a two-dimensional image is formed based on a method obtained by the two-dimensional scanning (for example, refer to patent document 1).

Patent document 1: Japanese Patent Laid-Open No. 2000-139906 (paragraphs 0009 and 0010 and FIGS. 2 and 4)

DISCLOSURE OF THE INVENTION

Problems to be Solved by the Invention

However, in the conventional ultrasonic diagnostic apparatus, there is a problem in that two-dimensional (main) scanning cannot be performed while three-dimensional (sub) scanning is performed.

The invention is embodied for solving the problem in the related art and it is an object of the invention to provide an ultrasonic diagnostic apparatus that can perform main scanning in a main scan region while performing subscanning in a subscan region and performs the main scanning of the main scan region of a region of interest at high speed and the subscanning of the subscan region of other regions at low speed.

Means For Solving the Problems

An ultrasonic diagnostic apparatus of the invention has the configuration wherein a scan region is divided into a main scan region and a subscan region and the main scan region and the subscan region are made up of two-dimensional scan regions or three-dimensional scan regions and the subscan region is divided into a plurality of small regions and main scanning of the main scan region is performed between subscanning of one small region and subscanning of another small region.

According to the configuration, main scanning of the main scan region can be performed while subscanning of the subscan region is performed, and the main scanning of the main scan region of the region of interest cab be performed at high speed and the subscanning of the subscan region of other regions cab be performed at low speed.

The ultrasonic diagnostic apparatus of the invention has the configuration wherein in the whole scan region made up of the main scan region and the subscan region, the main scan region is main-scanned at equal time intervals regardless of where the main scan region is placed in the whole scan region.

According to the configuration, if the tissue in the main scan region displaces on the time base, it becomes easy to keep track of the time displacement.

Further, the ultrasonic diagnostic apparatus of the invention has the configuration wherein the scan region spreads to a two-dimensional or three-dimensional region and a plurality of scan regions exist.

According to the configuration, when the region of interest exists in a plurality of two-dimensional or three-dimensional regions, the scanning rate of the main scan region of the region of interest can be increased.

Further, the ultrasonic diagnostic apparatus of the invention has the configuration wherein the plurality of scan regions cross each other.

According to the configuration, if a plurality of scan regions cross each other, the scanning rate of the main scan region of the region of interest can be increased.

Further, the ultrasonic diagnostic apparatus of the invention has the configuration wherein the number of irradiation times with a transmission ultrasonic beam per unit time is made different in the subscan region.

According to the configuration, the subscanning rate of the region of comparatively high interest in the subscan region can be increased.

Further, the ultrasonic diagnostic apparatus of the invention has the configuration wherein it has a scan converter for updating a display image in real time upon each completion of transmission ultrasonic beam scanning made up of the main scanning of the main scan region multiple times and the subscanning of the subscan region in the scan region, and the scan converter can set different persistence in the main scan region and the subscan region.

According to the configuration, the scanning speed of the transmission ultrasonic beam in the scan region and the image update speed of a display can be matched with each other.

Further, the ultrasonic diagnostic apparatus of the invention has the configuration a marker is displayed on a boundary between the main scan region and the subscan region.

According to the configuration, the boundary between the main scan region and the subscan region can be clearly identified.

Advantages of the Invention

The invention can provide the ultrasonic diagnostic apparatus having the advantage that it can perform main scanning of the main scan region between subscanning of one subscan region and subscanning of another subscan region, can continue the main scanning of the main scan region of the region of interest, and can perform the main scanning of the region of interest at high speed and subscanning of other regions at low speed by providing the configuration wherein the scan region is divided into the main scan region and the subscan region and the subscan region is divided into. the small regions and the main scanning of the main scan region is performed between subscanning of one small region and subscanning of another small region.

BRIEF DESCRIPTION OF THE DRAWINGS

FIG. 2 is a drawing to show an outline of scanning of an ultrasonic diagnostic apparatus in a second embodiment of the invention, a scan region, and scanning timings.

FIG. 3 is a drawing to show an outline of scanning of an ultrasonic diagnostic apparatus in a third embodiment of the invention and scanning timings.

DESCRIPTION OF REFERENCE NUMERALS

1 Two-dimensional array probe
Am Main scan region
As1 Small region
As2 Small region
As3 Small region
As4 Small region
2 Scan converter
3 Display section
4 Memory

BEST MODE FOR CARRYING OUT THE INVENTION

Figure 1A:
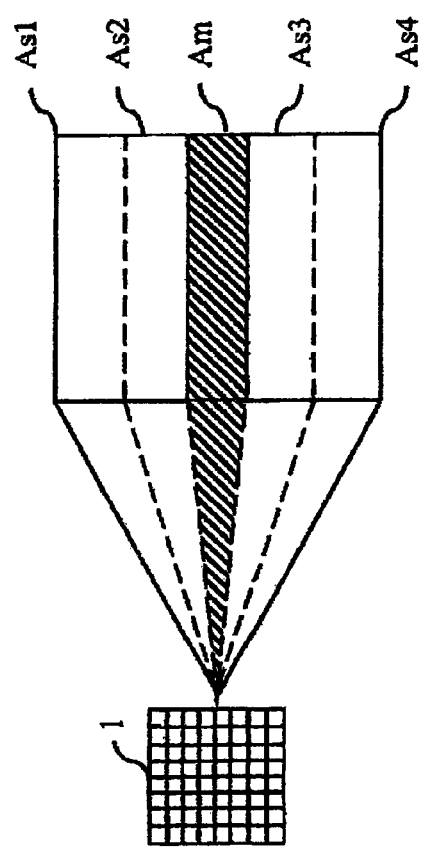
FIG. 1 is a drawing to show an outline of scanning of an ultrasonic diagnostic apparatus in a first embodiment of the invention and scanning timings.
Figure 1B:
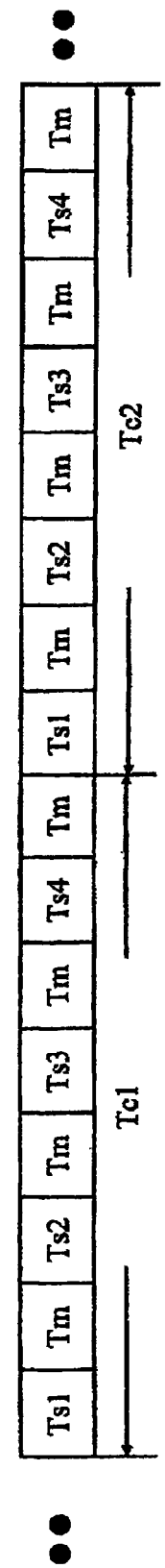

An ultrasonic diagnostic apparatus of each embodiment of the invention will be discussed below with the accompanying drawings:

FIG. 1A shows an outline of scanning in the ultrasonic diagnostic apparatus of a first embodiment of the invention and FIG. 1B shows scanning timings.

In FIG. 1A, a two-dimensional array probe 1 formed by arranging a plurality of ultrasonic elements two-dimensionally transmits an ultrasonic beam to a three-dimensional region and receives a reflected signal. The ultrasonic beam scans a region on a pyramid, and the scan region is divided into a main scan region Am of a region of interest and a subscan region. The subscan region is divided into small regions As1, As2, As3, and As4. In FIG. 1B, the main scanning time of the main scan region Am is indicated as Tm, the subscanning time of the small region As1 is indicated as Ts1, the subscanning time of the small region As2 is indicated as Ts2, the subscanning time of the small region As3 is indicated as Ts3, and the subscanning time of the small region As4 is indicated as Ts4.

The operation of the ultrasonic diagnostic apparatus configured as described above will be discussed with FIGS. 1A and 1B.

To begin with, the small region As1 is subscanned at the time Ts1. Next, the main scan region Am is main-scanned at the time Tm. Next, the small region As2 is subscanned at the time Ts2. Next, the main scan region Am is main-scanned at the time Tm. Next, the small region As3 is subscanned at the time Ts3. Next, the main scan region Am is main-scanned at the time Tm. Next, the small region As4 is subscanned at the time Ts4. Next, the main scan region Am is main-scanned at the time Tm. Scanning the scan region is completed in a time Tc1. Thus, while the whole scan region is scanned once, the main scan region Am of the region of interest can be main-scanned four times. Also in a time Tc2, scanning is performed in a similar manner. Thus, it is also made possible to main-scan the main scan region Am of the region of interest at equal intervals during the scan region is scanned.

According to the ultrasonic diagnostic apparatus of the first embodiment of the invention, the scan region is divided into the main scan region Am of the region of interest and the subscan region and the subscan region is. divided into the small regions As1, As2, As3, and As4, whereby the main scan region Am of the region of interest can be main-scanned multiple times while the whole scan region is scanned once. It is also made possible to main-scan the main scan region Am of the region of interest at equal intervals during the scan region is scanned, and if the tissue in the main scan region displaces on the time base, it becomes easy to keep track of the time displacement.

Next, FIG. 2A shows an outline of scanning in an ultrasonic diagnostic apparatus of a second embodiment of the invention, FIG. 2B shows scan regions, and FIG. 2C shows scanning timings.

In FIG. 2A, a plurality of scan regions exist as scan regions R1 and R2. The scan regions R1 and R2 cross each other. In FIG. 2B, the scan region R1 is divided into a main scan region Am and a subscan region and the subscan region is divided into small scan regions As1 and As2. The scan region R2 is divided into a main scan region am and a subscan region and the subscan region is divided into small scan regions as1 and as2. In FIG. 2C, the main scanning time of the main scan region Am is indicated as Tm, the subscanning time of the small region As1 is indicated as Ts1, the subscanning time of the small region As2 is indicated as Ts2, the main scanning time of the main scan region am is indicated as tm, the subscanning time of the small region as1 is indicated as ts1, and the subscanning time of the small region as2 is indicated as ts2.

The operation of the ultrasonic diagnostic apparatus configured as described above will be discussed with FIGS. 2B and 2C.

To begin with, the small region As1 is subscanned at the time Ts1. Next, the main scan region Am is main-scanned at the time Tm. Next, the small region As2 is subscanned at the time Ts2. Next, the main scan region Am is main-scanned at the time Tm. Scanning the scan region R1 is thus completed. Next, the small region as1 is subscanned at the time ts1. Next, the main scan region am is main-scanned at the time tm. Next, the small region as2 is subscanned at the time ts2. Next, the main scan region am is main-scanned at the time am. Scanning the scan region R2 is thus completed. Thus, while the scan regions R1 and R2 are scanned each once in a time Tc1, the main scan regions Am and am of regions of interest can be main-scanned twice. Also in a time Tc2, scanning is performed in a similar manner. In FIG. 2C, the main scan regions are main-scanned in the order of Am, Am, am, and am, but can also be main-scanned in the order of Am, am, Am, and am. Thus, it is also made possible to main-scan the main scan regions Am and am of the regions of interest at equal intervals.

As described above, according to the ultrasonic diagnostic apparatus of the second embodiment of the invention, a plurality of scan regions exist as the scan regions R1 and R2, the scan regions R1 and R2 cross each other, the scan region R1 is divided into the main scan region Am and the subscan region, the subscan region is divided into the small scan regions As1 and As2, the scan region R2 is divided into the main scan region am and the subscan region, and the subscan region is divided into the small scan regions as1 and as2, whereby the main scan regions Am and am of the regions of interest can be main-scanned twice while the scan regions R1 and R2 are scanned each once.

Next, FIG. 3A shows an outline of scanning in an ultrasonic diagnostic apparatus of a third embodiment of the invention and FIG. 3B shows scanning timings.

In FIG. 3A, a scan region R1 is divided into a main scan region Am and a subscan region and the subscan region is divided into small scan regions As1, As2, and As3. In FIG.

3B, the main scanning time of the main scan region Am is indicated as Tm, the subscanning time of the small region As1 is indicated as Ts1, the subscanning time of the small region As2 is indicated as Ts2, and the subscanning time of the small region As3 is indicated as Ts3.

The operation of the ultrasonic diagnostic apparatus configured as described above will be discussed with FIG. 3B.

To begin with, the small region As1 is subscanned at the time Ts1. Next, the main scan region Am is main-scanned at the time Tm. Next, the small region As2 is subscanned at the time Ts2. Next, the main scan region Am is main-scanned at the time Tm. Next, the small region As1 is subscanned at the time Ts1. Next, the main scan region Am is main-scanned at the time Tm. Next, the small region As2 is subscanned at the time Ts2. Next, the main scan region Am is main-scanned at the time Tm. Next, the small region As3 is subscanned at the time Ts3. Next, the main scan region Am is main-scanned at the time Tm. Scanning the scan region R1 is completed in a time Tc1. Thus, while the scan region R1 is scanned once, the main scan region Am of a region of interest can be main-scanned four times and further the number of irradiation times with a transmission ultrasonic beam per unit time is made different in the subscan region, whereby the small scan regions As1 and As2 of the subscan region can be subscanned each twice and the small scan region As3 of the subscan region can be subscanned once. Also in a time Tc2, scanning is performed in a similar manner. Thus, the subscanning rate of the region of comparatively high interest in the subscan region can be increased.

As described above, according to the ultrasonic diagnostic apparatus of the third embodiment of the invention, the number of irradiation times with a transmission ultrasonic beam per unit time is made different in the subscan region, whereby the subscanning rate of each of the small scan regions As1 and As2 of comparatively high interest in the subscan region can be made higher than that of the small scan region As3 of the subscan region.

Figure 4A:
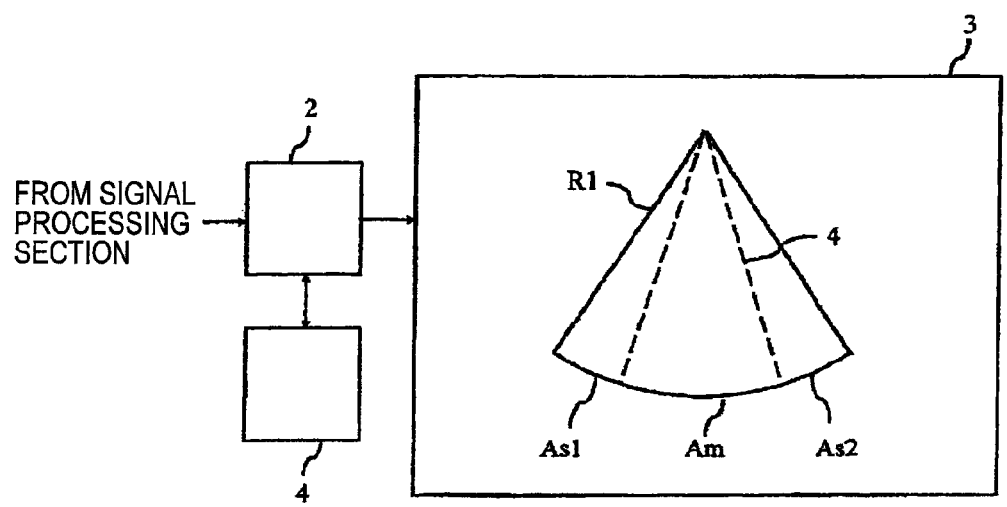
FIG. 4 is a block diagram of a display section of an ultrasonic diagnostic apparatus in a fourth embodiment of the invention and is a drawing to show scanning timings.
Figure 4B:
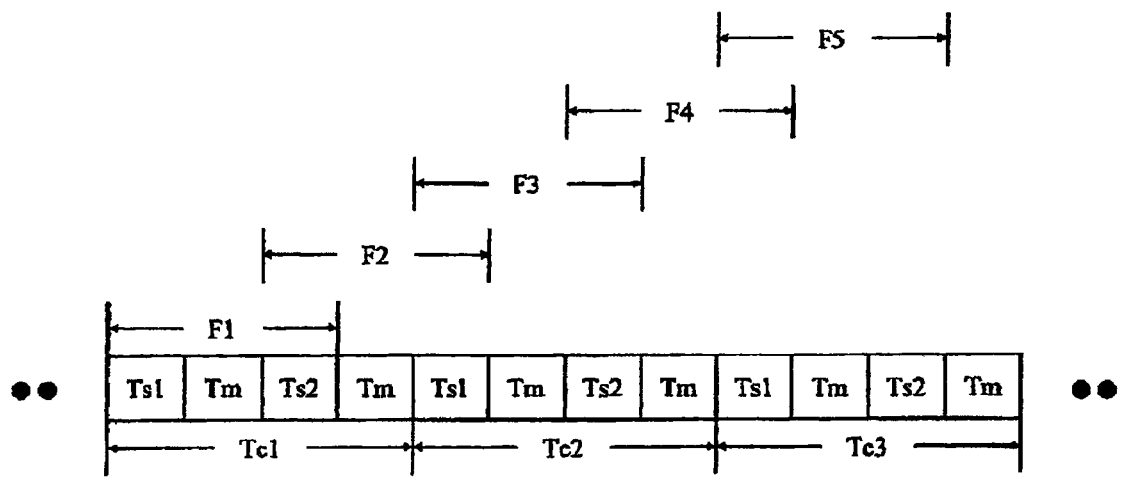
Figure 5A:
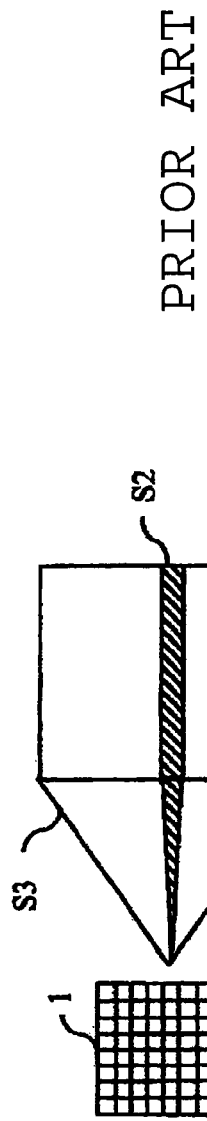
FIG. 5 is a drawing to show an outline of scanning of a conventional ultrasonic diagnostic apparatus and scanning timings.
Figure 5B:
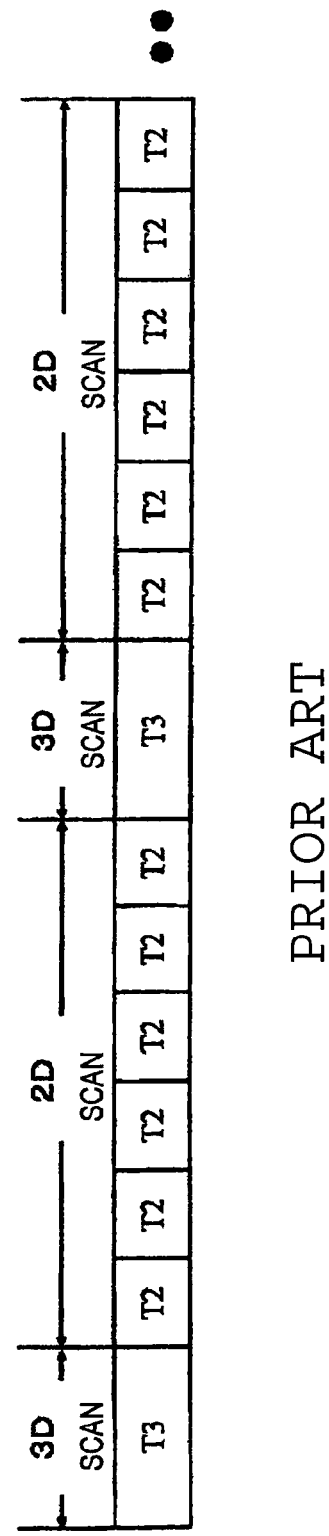

FIG. 4A shows blocks including a display section of an ultrasonic diagnostic apparatus of a fourth embodiment of the invention and FIG. 4B shows scanning timings.

In FIG. 4A, a reception signal from a two-dimensional array resonator is converted into an image signal in a scan converter 2. The image signal of the scan converter 2 is stored in memory 4. The image signal of the scan converter 2 is displayed on a display section 3. A scan region R1 is displayed on the display section 3. The scan region R1 is divided into a main scan region Am and a subscan region and the subscan region is divided into small scan regions As1 and As2. A marker 4 is displayed on each boundary between the main scan region Am and the subscan region, namely, the boundary between the main scan region Am and the small scan region As1 and the boundary between the main scan region Am and the small scan region As2. In FIG. 4B, the main scanning time of the main scan region Am is indicated as Tm, the subscanning time of the small region As1 is indicated as Ts1, and the subscanning time of the small region As2 is indicated as Ts2.

The operation of the ultrasonic diagnostic apparatus configured as described above will be discussed with FIGS. 4A and 4B.

To begin with, the small region As1 is subscanned at the time Ts1. Next, the main scan region Am is main-scanned at the time Tm. Next, the small region As2 is subscanned at the time Ts2. Next, the main scan region Am is main-scanned at the time Tm. Thus, the main scan region Am of a region of interest can be main-scanned twice while the whole scan region is scanned once. Also in a time Tc2, scanning is performed in a similar manner. The image data at the time Ts1, the image data at the time Tm, and the image data at the time Ts2 form an image frame F1. Likewise, the image data at the time Ts2, the image data at the time Tm, and the image data at the time Ts1 form an image frame F2. Frames F3, F4, and F5 are formed in such a manner. The formed frames are stored in the memory 4. On the other hand, the display section produces display at the intervals of the times Tc1 and Tc2. The frames F1, F3, and F5 are displayed in real time in scanning the region R1. However, since all frames are stored in the memory 4, if the image read speed from the memory 4 is decreased, all image frames can be displayed on the display section 3.

In the scan converter 2, persistence (afterimage effect) can also be given to an image Vm in the main scan region Am and images Vs1 and Vs2 in the small regions As1 and As2 of the subscan region. In this case, comparatively strong persistence may be given to the main scan region because the number of main scanning times per unit time is large, and comparatively weak persistence may be given to the subscan region because the number of subscanning times per unit time is small. Alternatively, if the tissue in the main scan region displaces largely on the time base, comparatively weak persistence may be given to the main scan region and comparatively strong persistence may be given to the subscan region.

As described above, according to the ultrasonic diagnostic apparatus of the fourth embodiment of the invention, the scan converter is provided for updating the display image in real time upon each completion of transmission ultrasonic beam scanning made up of the main scanning of the main scan region multiple times and the subscanning of the subscan region in the scan region, whereby the scanning speed of the transmission ultrasonic beam in the scan region and the image update speed of the display can be matched with each other.

Further, in the ultrasonic diagnostic apparatus of the invention, the image persistence corresponding to the main scan region is made different from the image persistence corresponding to the subscan region, whereby image display suited for high-speed displacement of the tissue in the region of interest of the main scan region and low-speed displacement of the tissue in the subscan region can be produced.

In the embodiments described above, if both the main scan region and the subscan region are obtained by two-dimensional scanning and the two-dimensional scanning faces are on the same plane, the probe 1 may be a one-dimensional array.

While the invention has been described in detail with reference to the specific embodiments, it will be obvious to those skilled in the art that various changes and modifications can be made without departing from the spirit and the scope of the invention.

This application is based on Japanese Patent Application (No. 2006-245223) filed on Sep. 11, 2006, which is incorporated herein by reference.

Industrial Applicability

As described above, the scan region is divided into the main scan region and the subscan region and the subscan region is divided into the small regions and main scanning of the main scan region is performed between subscanning of one small region and subscanning of another small region, whereby the ultrasonic diagnostic apparatus according to the invention has the advantage that main scanning of the main scan region can be performed between subscanning of one subscan region and subscanning of another subscan region and the main scanning of the main scan region of the region of interest can be continued, and is useful as an ultrasonic diagnostic apparatus for scanning the region of interest at high speed and other regions at low speed or the like.

The invention claimed is:

1. An ultrasonic diagnostic apparatus, wherein a whole scan region is divided into a main scan region and a subscan region, the subscan region is divided into a plurality of small regions, the main scan region and the subscan region are, respectively, made up of a two-dimensional scan region or and a three-dimensional scan region, and each main scan of the main scan region is performed, in an alternating pattern, between a subscan of one small region of the subscan region and a subscan of another small region of the subscan region, wherein, in the whole scan region made up of the main scan region and the subscan region, the main scan region is main-scanned at equal time intervals regardless of where the main scan region is placed in the whole scan region, and wherein the whole scan region spreads to a two-dimensional or three-dimensional region and a plurality of scan regions exist.

2. The ultrasonic diagnostic apparatus as claimed in claim 1 wherein the plurality of scan regions cross each other.

3. The ultrasonic diagnostic apparatus as claimed in any of claims 1 or 2 wherein the number of irradiation times with a transmission ultrasonic beam per unit time is made different between one or more small regions in the subscan region.

4. The ultrasonic diagnostic apparatus as claimed in claim 1 having a scan converter for updating a display image in real time upon each completion of transmission ultrasonic beam scanning made up of the main scanning of the main scan region multiple times and the subscanning of the subscan region in the whole scan region, wherein the scan converter can set different persistence in the main scan region and the subscan region.

5. The ultrasonic diagnostic apparatus as claimed in claim 4 wherein a marker is displayed on a boundary between the main scan region and the subscan region.

* * * * *